(12) United States Patent
Sugita et al.

(10) Patent No.: US 7,148,011 B2
(45) Date of Patent: Dec. 12, 2006

(54) METHOD OF TESTING FOR ALLERGIC DISEASES

(75) Inventors: Yuji Sugita, Saitama (JP); Ryoichi Hashida, Ibaraki (JP); Kaoru Ogawa, Ibaraki (JP); Tomoko Fujishima, Tokyo (JP); Takeshi Nagasu, Ibaraki (JP); Gozoh Tsujimoto, Tokyo (JP); Eiki Takahashi, Chiba (JP)

(73) Assignees: Japan as represented by General Director of Agency of National Center for Child Health and Development, Tokyo (JP); Eisai Co., Ltd., Tokyo (JP); Genox Research, Inc., Ibaraki (JP)

( * ) Notice: Subject to any disclaimer, the term of this patent is extended or adjusted under 35 U.S.C. 154(b) by 358 days.

(21) Appl. No.: 10/380,254

(22) PCT Filed: Sep. 21, 2001

(86) PCT No.: PCT/JP01/08246

§ 371 (c)(1),
(2), (4) Date: Jul. 31, 2003

(87) PCT Pub. No.: WO02/24903

PCT Pub. Date: Mar. 28, 2002

(65) Prior Publication Data

US 2004/0038252 A1 Feb. 26, 2004

(30) Foreign Application Priority Data

Sep. 25, 2000 (JP) .............................. 2000-291318

(51) Int. Cl.
*C12Q 1/68* (2006.01)

(52) U.S. Cl. ........................................ 435/6

(58) Field of Classification Search ..................... None
See application file for complete search history.

(56) References Cited

U.S. PATENT DOCUMENTS

2003/0143589 A1 * 7/2003 Baughn et al. ................ 435/6

FOREIGN PATENT DOCUMENTS

| JP | 11-332567 A | 12/1999 |
|----|-------------|---------|
| WO | WO 00/20571 A1 | 4/2000 |
| WO | WO 00/20575 A1 | 4/2000 |
| WO | WO 00/65046 A1 | 11/2000 |
| WO | WO 02/26962 A1 | 4/2002 |

OTHER PUBLICATIONS

Hillier et al. "Generation and Analysis of 280,00 human expressed sequence tags", Genome Research, 1996, 6, 807-828.*
Sequence alignment—Result 4, Baughn et al., p. 5-7.*
Hillier et al., "Generation and Analysis of 280,000 Human Expressed Sequence Tags," *Genome Res.* 6:807-828 (1996).
Ito et al., "Fluorescent Differential Display: Arbitrarily Primed RT-PCT Fingerprinting on an Automated DNA Sequencer," *FEBS Letters* 351:231-236 (1994).
Liang et al., "Differential Display of Eukaryotic Messenger RNA by Means of the Polymerase Chain Reaction," *Science* 257:967-971 (1992).

* cited by examiner

*Primary Examiner*—Gary Renzion
*Assistant Examiner*—Stephanie Mummert
(74) *Attorney, Agent, or Firm*—Klarquist Sparkman, LLP

(57) ABSTRACT

The differential display method was used to search for a gene whose expression level in eosinophils collected from patients with atopic dermatitis differs in the exacerbation stage and in the remission stage. As a result, gene "2090-05" showing a significant increase in expression in eosinophils of patients in the remission stage was isolated. This gene is usable in testing for an allergic disease and screening for a candidate compound for a therapeutic agent therefor an allergic disease.

4 Claims, 2 Drawing Sheets

2090-05

B : Brain
H : Heart
SM : Skeletal Muscle
Co : Colon
Th : Thymus
Sp : Spleen
K : Kidney
Li : Liver
SL : Small Intestine
P : Placenta
L : Lung
PBL: Peripheral Blood Leukocyte

METHOD OF TESTING FOR ALLERGIC DISEASES

CROSS-REFERENCE TO RELATED APPLICATIONS

This is a § 371 national stage of PCT/JP01/08246, filed Sep. 21, 2001, which in turn claims the benefit of Japanese Application No. 2000-291318 filed Sep. 25, 2000.

TECHNICAL FIELD

The present invention relates to genes associated with allergic diseases, methods of testing for allergic diseases and methods of screening for compounds that serve as candidate therapeutic agents for allergic diseases using the expression of the genes as an indicator.

BACKGROUND ART

Allergic diseases such as atopic dermatitis are considered to be multifactorial diseases. These diseases are caused by the interaction of many different genes, whose expressions are influenced by several various environmental factors. Thus, determination of specific genes causing a specific disease has been extremely difficult for allergic diseases.

Additionally, expression of mutated or defective genes, or overexpression or reduced expression of specific genes is thought to be involved in allergic diseases. To elucidate the role of gene expression in diseases, it is necessary to understand how a gene is involved in triggering disease onset and how the expression of the gene is altered by external stimulants such as drugs.

Recent developments in gene expression analysis techniques have enabled analysis and comparison of gene expression of many clinical samples. Among these methods, the differential display (DD) method is useful. The differential display method was originally developed by Liang and Pardee in 1992 (Science, 1992, 257: 967–971). According to this method, several tens or more different samples can be screened at one time to detect genes whose expressions are different among the samples. Important information to reveal the causative gene of a disease is expected by examining genes with mutations or genes whose expression changes depending on time and environment. Such genes include those whose expression is influenced by environmental factors.

History taking, and confirmation of family history and anamnesis of the patient are important in general for recent diagnosis of allergic diseases. Further, methods of diagnosing allergy based on more objective information include a method in which patient's blood sample are tested and method of observing patient's immune response to allergen. Examples of the former method are the allergen-specific IgE measurement, leukocyte histamine release test, and lymphocyte stimulating test. The presence of allergen-specific IgE verifies the allergic reaction against the allergen. However, allergen-specific IgE is not always detected in every patient. Furthermore, the principle of IgE assay requires performing tests for all of the allergens necessary for diagnosis. The leukocyte histamine release test and lymphocyte stimulating test are methods for observing the reaction of the immune system toward a specific allergen in vitro. These methods require complicated operation.

Another known method is allergy diagnosis based on the immune response observed at the time when a patient is contacted with an allergen (latter method). Such tests include the prick test, scratch test, patch test, intradermal reaction, and induction test. These tests allow direct diagnosis of patient's allergic reaction, but can be regarded as high invasive tests because patients are actually exposed to allergen.

In addition, regardless of the allergen types, methods to testify the involvement of allergic reaction are also attempted. For example, a high serum IgE titer indicates the occurrence of allergic reaction in a patient. The serum IgE titer is the information corresponding to the total amount of allergen-specific IgE. Though it is easy to determine the total amount of IgE regardless of the type of allergen, IgE titer may be reduced in some patients, for example, those with non-atopic bronchitis.

The number of eosinophils and eosinophil cationic protein (ECP) value are items for diagnosing delayed-type reaction following Type I allergy and allergic inflammatory reaction. The number of eosinophils is considered to reflect the progress of allergic symptoms. ECP, a protein contained in eosinophil granules, is also strongly activated in patients with an asthma attack. Even though these diagnostic items reflect allergy symptoms, their scope usable as the diagnostic indicator is limited.

Therefore, diagnostic indicators, regardless of the type of allergen, useful in comprehending pathological conditions of allergic disease patients and for determining the treatment regimen for the disease have been intensely desired in the art. Furthermore, markers for allergic disease that are less harmful to patients and easily provide information required for diagnosis will be of great use.

DISCLOSURE OF THE INVENTION

An objective of the present invention is to provide genes associated with allergic diseases. Another objective of the invention is to provide a method of testing for allergic diseases and a method of screening for compounds that serve as candidate therapeutic agents for allergic diseases using the expression of the genes of the present invention as an indicator.

Based on a previously established technique, the "Fluorescent differential display method (Fluorescent DD method)" (T. Ito et al. 1994, FEBS Lett. 351: 231–236), the present inventors developed a new DD system that analyzes T-cell RNA samples prepared from multiple human blood samples (WO 00/65046). The present inventors applied the DD system to the isolation of genes whose expression level is altered in an allergic disease-specific manner.

Specifically, the present inventors initially compared several parameters relating to allergic symptoms in the exacerbation stage and in the remission stage of dermatitis conditions of atopic dermatitis patients. As a result, decrease of eosinophils in the remission stage was observed in some of the patients. Since eosinophils generally serve as the typical clinical indicator for atopic dermatitis, the present inventors focused on this observation. They considered that a gene that is directly involved in atopic dermatitis may be isolated if a gene whose expression level in eosinophils from the same patient in the exacerbation stage differs from that in the remission stage, can be isolated.

Therefore, eosinophils were collected from several subjects in the exacerbation stage and in the remission stage of atopic dermatitis, and genes having varying expression levels in eosinophils were screened using the aforementioned system. As a result, a gene, "2090-05", showing a significant increase in the expression level in patients in the remission stage was successfully isolated. This gene was considered novel since the same nucleotide sequence could not be found in known genetic databases. Furthermore, the present inventors discovered that testing of an allergic disease, and screening of candidate compounds for a therapeutic agent for an allergic disease can be performed using the expression level of this gene as an indicator, and thereby completed this invention.

Specifically, this invention relates to a gene showing high levels of expression in the remission stage of atopic dermatitis, a protein encoded by this gene, and uses thereof. More specifically, this invention relates to a method of testing for an allergic disease using expression of the gene as an indicator, a method of detecting an influence of candidate compounds on expression of the gene, and in addition, a method of screening for candidate compounds for a therapeutic agent for an allergic disease based on this detection method.

[1] A method of testing for an allergic disease, said method comprising the steps of:
 a) measuring the expression level of a gene comprising the nucleotide sequence of SEQ ID NO: 1 in eosinophil cells of a test subject; and
 b) comparing the measured expression level to the expression level of the gene in eosinophil cells of a healthy subject.

[2] The testing method of [1], wherein the allergic disease is atopic dermatitis.

[3] The testing method of [1], wherein the expression level of a gene is measured by cDNA PCR.

[4] The testing method of [1], wherein the expression level of a gene is measured by detecting a protein encoded by the gene.

[5] A reagent for testing for an allergic disease, said reagent comprising an oligonucleotide that is at least 15 nucleotides long and comprises a nucleotide sequence complementary to a polynucleotide having the nucleotide sequence of SEQ ID NO: 1, or to its complementary strand.

[6] A reagent for testing for an allergic disease, said reagent comprising an antibody that recognizes a peptide having the amino acid sequence of SEQ ID NO: 2.

[7] A method of detecting an influence of a candidate compound on the expression level of a polynucleotide of any one of (a) to (d), said method comprising the steps of:
 (1) contacting the candidate compound with a cell that expresses a polynucleotide of any one of (a) to (d):
  (a) a polynucleotide comprising a coding region of the nucleotide sequence of SEQ ID NO: 1;
  (b) a polynucleotide encoding a protein comprising the amino acid sequence of SEQ ID NO: 2;
  (c) a polynucleotide encoding a protein that is functionally equivalent to a protein that shows increased expression in eosinophils in the remission stage of atopic dermatitis, and comprising an amino acid sequence of SEQ ID NO: 2 in which one or more amino acids have been substituted, deleted, inserted, and/or added; and
  (d) a polynucleotide encoding a protein that shows increased expression in eosinophils in the remission stage of atopic dermatitis, wherein said polynucleotide hybridizes under stringent conditions with a DNA comprising the nucleotide sequence of SEQ ID NO: 1; and
 (2) measuring the expression level of the polynucleotide of any one of (a) to (d) of (1).

[8] The method of [7], wherein the cell is a leukocyte cell line.

[9] A method of detecting an influence of a candidate compound on the expression level of a polynucleotide of any one of (a) to (d):
 (a) a polynucleotide comprising a coding region of the nucleotide sequence of SEQ ID NO: 1;
 (b) a polynucleotide encoding a protein comprising the amino acid sequence of SEQ ID NO: 2;
 (c) a polynucleotide encoding a protein that is functionally equivalent to a protein that shows increased expression in eosinophils in the remission stage of atopic dermatitis, and comprising an amino acid sequence of SEQ ID NO: 2 in which one or more amino acids have been substituted, deleted, inserted, and/or added; and
 (d) a polynucleotide encoding a protein that shows increased expression in eosinophils in the remission stage of atopic dermatitis, wherein said polynucleotide hybridizes under stringent conditions with a DNA comprising the nucleotide sequence of SEQ ID NO: 1; said method comprising the steps of:
 (1) administering the candidate compound to a test animal; and
 (2) measuring the expression intensity of the polynucleotide of any one of (a) to (d) in the eosinophil cells of the test animal.

[10] A method of screening for a compound that raises the expression level of the polynucleotide of any one of (a) to (d) above, the method comprising the steps of detecting an influence on the expression level by the method of [7] or [9], and selecting a compound that raises the expression level compared to a control.

[11] A method of detecting an influence of a candidate compound on the activity of a transcription regulatory region of a gene comprising the nucleotide sequence of SEQ ID NO: 1, said method comprising the steps of:
 (1) contacting a candidate compound with a cell transfected with a vector comprising the transcription regulatory region of the gene containing the nucleotide sequence of SEQ ID NO: 1, and a reporter gene that is expressed under the control of the transcription regulatory region; and
 (2) measuring the activity of the reporter gene.

[12] A method of screening for a compound that raises the activity of the transcription regulatory region of a gene containing the nucleotide sequence of SEQ ID NO: 1, said method comprising the steps of detecting an influence of a candidate compound on the activity by the method of [11], and selecting a compound that raises the activity compared to a control.

[13] A vector comprising the transcription regulatory region of a gene containing the nucleotide sequence of SEQ ID NO: 1, and a reporter gene that is expressed under the control of the transcription regulatory region.

[14] A cell carrying the vector of [13].

[15] A therapeutic agent for an allergic disease, said agent comprising as the active ingredient, a compound obtainable by the method of screening of [10] or [12].

[16] A polynucleotide of any one of (a) to (d):
 (a) a polynucleotide comprising a coding region of the nucleotide sequence of SEQ ID NO: 1,
 (b) a polynucleotide encoding a protein comprising the amino acid sequence of SEQ ID NO: 2,
 (c) a polynucleotide encoding a protein that is functionally equivalent to a protein that shows increased expression in eosinophils in the remission stage of atopic dermatitis, and comprising an amino acid sequence of SEQ ID NO: 2 in which one or more amino acids have been substituted, deleted, inserted, and/or added, and
(d) a polynucleotide encoding a protein that shows increased expression in eosinophils in the remission stage of atopic dermatitis, wherein said polynucleotide hybridizes under stringent conditions with a DNA comprising the nucleotide sequence of SEQ ID NO: 1.

[17] A protein encoded by the polynucleotide of [16].

[18] A vector that harbors the polynucleotide of [16] in an expressible state.

[19] A transformed cell that harbors the polynucleotide of [16], or the vector of [18].

[20] A method of producing the protein of [17], said method comprising the steps of culturing the transformed cell of [19], and collecting its expression product.

[21] An antibody against the protein of [17].

[22] A method of immunologically measuring the protein of [17], said method comprising the step of observing the immunological reaction between the antibody of [21] and the protein of [17].

[23] An oligonucleotide having at least 15 nucleotides long, and comprising a nucleotide sequence complementary to a polynucleotide having the nucleotide sequence of SEQ ID NO: 1, or to its complementary strand.

[24] A method of measuring the polynucleotide of [16], said method comprising the step of observing hybridization of the oligonucleotide of [23] to the polynucleotide of [16].

[25] An allergic disease model animal, wherein said animal is a transgenic non-human vertebrate, in which expression intensity of the polynucleotide of any one of (a) to (d) in eosinophil cells is diminished:
(a) a polynucleotide comprising a coding region of the nucleotide sequence of SEQ ID NO: 1;
(b) a polynucleotide encoding a protein comprising the amino acid sequence of SEQ ID NO: 2;
(c) a polynucleotide encoding a protein that is functionally equivalent to a protein that shows increased expression in eosinophils in the remission stage of atopic dermatitis, and comprising an amino acid sequence of SEQ ID NO: 2 in which one or more amino acids have been substituted, deleted, inserted, and/or added; and
(d) a polynucleotide encoding a protein that shows increased expression in eosinophils in the remission stage of atopic dermatitis, wherein said polynucleotide hybridizes under stringent conditions with a DNA comprising the nucleotide sequence of SEQ ID NO: 1.

[26] The model animal of [25], wherein the transgenic animal is a knockout animal.

[27] A kit for screening for a candidate compound for a therapeutic agent for an allergic disease, said kit comprising cells that express a gene comprising the nucleotide sequence of SEQ ID NO: 1, and a polynucleotide that is at least 15 nucleotides long and hybridizes to the nucleotide sequence of SEQ ID NO: 1 or to its complementary strand.

[28] A kit for screening for a candidate compound for a therapeutic agent for an allergic disease, said kit comprising cells that express a gene comprising the nucleotide sequence of SEQ ID NO: 1, and an antibody that recognizes the peptide comprising the amino acid sequence of SEQ ID NO: 2.

The present invention relates to a method of testing for an allergic disease using a novel gene, "2090-05", and the expression level of "2090-05" in eosinophil cells as indicators. "2090-05" is a gene that shows an increased expression level in the remission stage of atopic dermatitis patients. The "2090-05" gene of this invention was considered novel because no particular gene with high structural identity thereto could be found. "2090-05" comprises the nucleotide sequence of SEQ ID NO: 1.

"2090-05" contains at the 5' side a region estimated to be a part of an ORF (1-561) encoding 187 amino acids. This amino acid sequence had 50% to 74% homology to acetyltransferases of *Drosophila melanogaster, Caenorhabditis elegans, Arabidopsis thaliana, Schizosaccharomyces pombe*, and *Saccharomyces cerevisiae*. The homology to the amino acid sequence of these proteins is as follows.

*Drosophila melanogaster*/Acetyltransferase
 : 74% identity in 137 aa
*Caenorhabditis elegans*/Acetyltransferase
 : 61% identity in 149 aa
*Arabidopsis thaliana*/Putative Acetyltransferase
 : 56% identity in 154 aa
*Schizosaccharomyces pombe*/N-Acetyltransferase
 : 50% identity in 141 aa
*Saccharomyces cerevisiae*/N-Acetyltransferase
 : 51% identity in 145 aa Among these proteins, functional analysis has been reported for only N-acetyltransferase of *S. cerevisiae*. In many other reports, these proteins are putative proteins predicted from their genomic sequences, and considered as acetyltransferase based on their homology to N-acetyltransferase of *S. cerevisiae* and PFAM domain PF00583 (acetyltransferase). At any rate, there is no report on the relationship between these genes and allergic diseases. The present inventors found for the first time that "2090-05" comprising the nucleotide sequence of SEQ ID NO: 1 is involved in allergic diseases.

The nucleotide sequence shown in SEQ ID NO: 1 is a partial sequence of the full length cDNA. The full length cDNA containing this partial sequence can be obtained by screening a cDNA library of leukocytes with a probe comprising a nucleotide sequence selected from the nucleotide sequence of SEQ ID NO: 1. "2090-05" is expressed not only in eosinophils but also in basophils. Therefore, either one of the cDNA library derived from these cells, or from a group of cells comprising these cells can be used to obtain the "2090-05" gene of this invention. Furthermore, the sequence of "2090-05" can be extended by the RACE method (Frohman, M. A. et al.: Proc. Natl. Acad. Sci. USA, 85: 8992, 1988). Specifically, extended cDNA can be obtained by using the sequence derived from "2090-05" as a primer, converting the mRNA of leukocytes and such into single stranded cDNA, adding an oligomer to its terminal end, then performing PCR.

A full length cDNA of "2090-05", which may be isolated in this manner based on the sequence information of the "2090-05" cDNA of SEQ ID NO: 1, is included in "a polynucleotide comprising the nucleotide sequence of SEQ ID NO: 1" of this invention. Furthermore, based on the nucleotide sequence of cDNA obtained in this manner, the amino acid sequence encoded by the cDNA can be estimated.

This invention relates to a polynucleotide comprising the nucleotide sequence of SEQ ID NO: 1. This invention also relates to a polynucleotide that hybridizes under stringent conditions to the polynucleotide comprising the nucleotide sequence of SEQ ID NO: 1 and that encodes a protein functionally equivalent to the protein encoded by the polynucleotide comprising the nucleotide sequence of SEQ ID NO: 1. In this invention, polynucleotide includes a natural nucleic acid molecule such as DNA and RNA, and artificial molecules comprising labeled molecule and various nucleotide derivatives. Artificial polynucleotides include polynucleotides having the phosphorothioate bond and peptide bond as a backbone.

These polynucleotides according to this invention can be chemically synthesized, or isolated from natural nucleic acids such as mRNA, a cDNA library, or a genomic library. Polynucleotide molecules according to this invention are useful for the production of protein encoded by them, inhibiting the "2090-05" expression as antisense nucleic acids, or as the probes for detecting their presence by hybridization.

Furthermore, in this invention, when expression of a certain protein increases in eosinophils in the remission stage of atopic dermatitis, this protein is said to be functionally equivalent to the protein of this invention. The increase in expression of a certain protein in eosinophils in the remission stage of atopic dermatitis can be confirmed by comparing the expression levels of the gene encoding this protein in eosinophils collected in the exacerbation stage and in the remission stage.

A polynucleotide that hybridizes under stringent conditions to the polynucleotide comprising the nucleotide sequence of SEQ ID NO: 1 and that encodes a functionally equivalent protein can be obtained by known techniques such as hybridization and PCR based on the nucleotide sequence of SEQ ID NO: 1. For example, cDNA comprising a nucleotide sequence that is highly homologous to that of SEQ ID NO: 1 can be obtained by screening a leukocyte cDNA library using an oligonucleotide comprising a nucleotide sequence selected from the nucleotide sequence of SEQ ID NO: 1 as a probe under stringent conditions. When a polynucleotide hybridizes to the polynucleotide comprising the nucleotide sequence of SEQ ID NO: 1 under stringent conditions, in most cases, such a protein encoded by the polynucleotide is thought to have the activity similar to that of the protein of this invention. Stringent conditions mean hybridization in 4×SSC at 65° c. followed by washing with 0.1×SSC at 65° c. for 1 hour. Temperature conditions for hybridization and washing that greatly influence stringency can be adjusted according to the melting temperature (Tm). Tm is varied with the ratio of constitutive nucleotides in the hybridizing base pairs, and the composition of hybridization solution (concentrations of salts, formamide, and sodium dodecyl sulfate). Therefore, considering these conditions, those skilled in the art can select an appropriate condition to produce an equal stringency from their experience.

A protein encoded by cDNA comprising the nucleotide sequence that has a high identity to the cDNA of this invention would be a functionally equivalent protein in this invention. Herein, a nucleotide sequence with a high identity refers to a nucleotide sequence that shows 75% or more homology in general, usually 80% or more, preferably 90% or more, more preferably 95% or more, furthermore preferably 98% or more, and specifically preferably 99% or more identity with the nucleotide sequence of this invention. The degree of identity of one nucleotide sequence to another can be determined by following the well-known algorism such as BLASTN.

Alternatively, cDNA with a high identity with cDNA of this invention can be obtained by PCR performed using oligonucleotides comprising the nucleotide sequence of SEQ ID NO: 1 as the primers and a leukocyte cDNA library as a template. If human cells are used as a source of cDNA, it is possible to obtain human cDNA. When cells from vertebrates other than humans are used, it is possible to obtain the counterpart of human cDNA in different animal species. Examples of such non-human animals are various experimental animals such as mice, rats, dogs, pigs, and goats. Counterparts of "2090-05" in experimental animals are useful in preparing allergic disease animal models from various animal species and as the marker in developing therapeutic agents for allergic diseases.

A gene encoding a protein having, for example, 90% or more, preferably 95% or more, and furthermore preferably 99% or more homology to the amino acid sequence of "2090-05" protein can be referred to as a gene functionally equivalent to the "2090-05" gene. A gene that can be amplified using, as primers, oligonucleotides comprising nucleotide sequences selected from the sequence of SEQ ID NO: 1 used in Examples and that encodes a protein whose expression increases in eosinophils in the remission stage of atopic dermatitis is also a functionally equivalent gene. In this invention, the "2090-05" gene or a gene functionally equivalent thereto is referred to as an indicator gene. A protein encoded by the indicator gene is termed an indicator protein.

The polynucleotides of this invention include those encoding proteins comprising the amino acid sequence of SEQ ID NO: 2 in which one or more amino acids are substituted, deleted, added and/or inserted, and which encode proteins functionally equivalent to the protein of this invention. For example, polymorphism is often observed among genes of eukaryotes. In some cases, one or more amino acids may be substituted by polymorphism, but usually the original activity of the protein is retained. It is also known that, even by the modification of one or several amino acids in an amino acid sequence, the protein activity is often retained. Therefore, all the polynucleotides, which encode proteins whose amino acid sequences are mutated by the modification of one or more amino acids through the artificial modification of the polynucleotide encoding the amino acid sequence of SEQ ID NO: 2, are included in this invention so far as these proteins have functions characteristic to those encoded by the gene of this invention. Preferably, such amino acid sequences include sequences that have 90% or more homology to the amino acid sequence of SEQ ID NO: 2. The homology of one amino acid sequence can be determined by FASTA.

Since codons for each amino acids are known, they may be arbitrarily selected and can be determined, for example, according to standard procedures considering the codon use frequency of the host to be employed (Grantham, R. et al. Nucleic Acids Res. 9, r43 (1981)). Therefore, DNAs appropriately modified considering the degeneracy of codons are also included in the polynucleotide of this invention. Codons in these nucleotide sequences can be partially modified according to the site-specific mutagenesis method (Mark, D. F. et al., Proc. Natl. Acad. Sci. U.S.A. 81, 5662 (1984)) or such using primers comprising synthetic oligonucleotides that encode the desired modification.

This invention also relates to an oligonucleotide that comprises a nucleotide sequence complementary to the polynucleotide having the nucleotide sequence of SEQ ID NO: 1 or to the complementary strand thereof, and that is at least 15-nucleotide-long. Herein, the term "complementary strand" is defined as one strand of a double strandedpolynucleotide composed of A:T (U for RNA) and G:C base pairs to the other strand. In addition, "complementary" strands may not be completely homologous within a region of at least 15 continuous nucleotides, and they have at least 70%, preferably at least 80%, more preferably 90%, and even more preferably 95% or higher homology within that region. The degree of homology of one nucleotide sequence to another can be determined by following the algorithm described in this specification.

The oligonucleotides of the present invention are useful for detecting and synthesizing the polynucleotide of this invention. Techniques for detecting or synthesizing the target nucleotide using oligonucleotides as the probe or primer are known. For example, Northern blot technique with mRNA as a target polynucleotide is a typical method of detecting RNA. RT-PCR that uses mRNA as a template enables the synthesis of the polynucleotide of this invention. Furthermore, it is also possible to find out the presence of mRNA as well as its expression level using the presence and amount of that synthetic product as an indicator. Alternatively, the polynucleotide of this invention that is expressed in eosinophils can be detected by an in situ hybridization technique.

Furthermore, using the polynucleotide of this invention, a protein encoded thereby can be produced as a recombinant. More specifically, a transformant is obtained by inserting the coding region of the polynucleotide having the nucleotide sequence of SEQ ID NO: 1 into a known expression vector, and transfecting an appropriate host with the resulting recombinant vector. Alternatively, a transformant is also obtained by integrating the polynucleotide containing the coding region into a genome of an appropriate host.

The protein of this invention can be obtained by culturing the resulting transformant under the conditions in which the polynucleotide of this invention can be expressed and collecting the expression product. The expression product can be purified by known techniques.

In addition, the present invention also relates to a protein encoded by the polynucleotide of this invention. The protein of this invention is useful as an indicator for diagnosing an allergic disease such as atopic dermatitis. Alternatively, since the polynucleotide of this invention shows increased expression in eosinophils in the remission stage, the protein itself that is encoded by this polynucleotide can be expected to show a therapeutic effect towards allergies.

Additionally, the protein of the present invention and its fragments are useful as the antigen for producing an antibody against the protein of this invention. Techniques for obtaining an antibody using a given antigen are known. That is, a protein or its fragment is mixed with an appropriate adjuvant, and the antigen thus prepared is inoculated to an animal to be immunized. There is no limitation in the type of animals to be immunized. Typical examples of animals to be immunized are mice, rats, rabbits, and goats. After the increase in the antibody titer is confirmed, blood is collected, and the serum is fractionated as an antiserum. The IgG fraction may be further purified to obtain a purified antibody. For the purification of antibody, techniques such as ammonium sulfate precipitation, ion exchange chromatography, immunoaffinity chromatography using protein A-conjugated Sepharose and the protein of this invention as the ligand can be utilized.

Furthermore, it is also possible to obtain amonoclonal antibody by transforming an antibody-producing cell using techniques such as cell fusion, and cloning the resulting transformant. Alternatively, a method of isolating a gene of the antibody-producing cell and constructing a humanized antibody and chimeric antibody is also known. The antibody thus obtained is useful as a tool for immunologically measuring the protein of this invention. The protein of the present invention can be immunologically assayed by contacting the protein of the invention with the antibody, and observing an immunological reaction between the two. Various known assay formats can be applied to the immunoassay according to this invention. For example, a protein contained in a sample such as serum can be measured by ELISA or such. Antibody-based detection of a protein expressed in eosinophils can be performed using immunohistochemical technique or fluorescence activated cell sorter (FACS) using a fluorescence labeled antibody.

Herein, the term "allergic disease" is a general term for diseases in which allergic reaction is involved. More specifically, it is defined as a disease in which an allergen must be identified, a strong correlation between the exposure to the allergen and the onset of the pathological change must be demonstrated, and the pathological change must be proven to have an immunological mechanism. Herein, an immunological mechanism means that immune responses by the leukocytes are induced by the stimulation of the allergen. Examples of allergens include mite antigen, and pollen antigen.

Representative allergic diseases include bronchial asthma, allergic rhinitis, atopic dermatitis, pollen allergy, and insect allergy. Allergic diathesis is a genetic factor that is inherited from allergic parents to their children. Familial allergic diseases are also called atopic diseases, and the causative factor that is inherited is the atopic diathesis. The term "atopic dermatitis" is a general term for atopic diseases with dermatitis among atopic diseases.

When the exacerbation stage and the remission stage in atopic dermatitis patients were compared, the "2090-05" gene of this invention showed increased expression level in the eosinophils of a patient in the remission stage. Therefore, allergic diseases can be tested using the expression level of the "2090-05" gene as an indicator.

The test for an allergic disease of this invention includes the following tests. For example, the present invention enables a test for deciding whether the allergic symptom is improving. The "2090-05" gene of this invention showed increased expression level especially in the eosinophils of atopic dermatitis patients in the remission stage. Since eosinophil is a representative clinical marker for atopic dermatitis, clinical marker expressed in eosinophils is useful for assessing therapeutic effects. More specifically, increased expression of the "2090-05" gene of this invention indicates that the allergic symptoms are improving.

Since the number of eosinophils and the severity of atopic dermatitis are closely related, if this gene that is induced specifically in eosinophils is measured, and if a method or substance that actively induces the gene from outside the cell is found, this may lead to a novel therapeutic method for atopic dermatitis and a diagnostic method for evaluating the therapeutic method.

Herein, the expression level of the "2090-05" gene includes the transcription of the gene to mRNA as well as the translation into protein. Therefore, a method for testing for allergic disease according to the present invention is performed by comparing the expression intensity of mRNA corresponding to the gene, or the expression level of a protein encoded by the gene.

Measurement of the expression level of the "2090-05" gene in a test for allergic diseases of the present invention may be conducted according to known gene analytical methods. More specifically, for example, a hybridization technique with a nucleic acid that hybridizes to the gene as a probe, a gene amplification technique with a DNA hybridizing to the gene of this invention as a primer, or such can be utilized.

As a primer or probe for the test according to the present invention can be used a polynucleotide comprising the nucleotide sequence of SEQ ID NO: 1 or at least 15 nucleotides that are complementary to the complementary strand thereof. Herein, the term "complementary strand" means one strand of a double stranded DNA composed of A:T (U for RNA) and G:C base pairs to the other strand. In addition, "complementary" means not only those completely complementary to a region of at least 15 continuous nucleotides, but also having a homology of at least 70%, preferably at least 80%, more preferably 90%, and even more preferably 95% or higher. The degree of homology between nucleotide sequences can be determined by the algorithm such as BLASTN.

Such polynucleotides can be useful as the probe to detect and isolate the polynucleotide encoding the protein according to the present invention, or as the primer to amplify the polynucleotide according to the present invention. When used as a primer, those polynucleotides comprise usually 15 bp to 100 bp, preferably 15 bp to 35 bp of nucleotides. When used as a probe, DNAs comprising the whole sequence of the polynucleotide according to the present invention, or a partial sequence thereof that contains at least 15-bp nucleotides. When used as a primer, the 3' region thereof must be complementary to the indicator gene, while the 5' region can be linked to a restriction enzyme-recognition sequence or tag.

The "polynucleotides" of the present invention may be either DNA or RNA. These polynucleotides may be either synthetic or naturally-occurring. Also, DNA used as a probe for hybridization is usually labeled. Examples of labeling methods are those as described below. Herein, the term "oligonucleotide" means a polynucleotide with relatively low degree of polymerization. Oligonucleotides are included in polynucleotides.

nick translation labeling using DNA polymerase I;
end labeling using polynucleotide kinase;
fill-in end labeling using Klenow fragment (Berger, S L, Kimmel, A R. (1987) Guide to Molecular Cloning Techniques, Method in Enzymology, Academic Press; Hames, B D, Higgins, S J (1985) Genes Probes: A Practical Approach. IRL Press; Sambrook, J, Fritsch, E F, Maniatis, T. (1989) Molecular Cloning: a Laboratory Manual, 2nd Edn. Cold Spring Harbor Laboratory Press);
transcription labeling using RNA polymerase (Melton, D A, Krieg, P A, Rebagkiati, M R, Maniatis, T, Zinn, K, Green, M R. (1984) Nucleic Acid Res., 12, 7035–7056); and
non-isotopic labeling of DNA by incorporating modified nucleotides (Kricka, L J. (1992) Nonisotopic DNA Probing Techniques. Academic Press).

For testing for an allergic disease using hybridization techniques, for example, Northern hybridization, dot blot hybridization, or DNA microarray technique may be used. Furthermore, gene amplification techniques, such as RT-PCR method may be used. By using the PCR amplification monitoring method during the gene amplification step in RT-PCR, one can achieve more quantitative analysis for the gene expression of the present invention.

In the PCR gene amplification monitoring method, the detection target (DNA or reverse transcript of RNA) is hybridized to probes that are dual-labeled at both ends with different fluorescent dyes whose fluorescences cancel each other out. When the PCR proceeds and Taq polymerase degrades the probe with its 5'-3' exonuclease activity, the two fluorescent dyes become distant from each other and the fluorescence becomes to be detected. The fluorescence is detected in real time. By simultaneously measuring a standard sample in which the copy number of the target is known, it is possible to determine the copy number of the target in the subject sample with the cycle number where PCR amplification is linear (Holland, P. M. et al., 1991, Proc. Natl. Acad. Sci. USA 88: 7276–7280; Livak, K. J. et al., 1995, PCR Methods and Applications 4(6): 357–362; Heid, C. A. et al., 1996, Genome Research 6: 986–994; Gibson, E. M. U. et al., 1996, Genome Research 6: 995–1001). For the PCR amplification monitoring method, for example, ABI PRISM7700 (PE Biosystems) may be used.

The method of testing for allergic diseases of the present invention can also be carried out by detecting a protein encoded by the "2090-05" gene. Such test methods are, for example, those utilizing antibodies binding to a protein encoded by this gene, including the Western blotting method, the immunoprecipitation method, and the ELISA method.

Antibodies that bind to the "2090-05" protein used in the detection may be produced by techniques known to those skilled in the art. Antibodies used in the present invention may be polyclonal or monoclonal antibodies (Milstein, C. et al., 1983, Nature 305 (5934): 537–40). For example, polyclonal antibodies against the protein of the present invention may be produced by collecting blood from mammals sensitized with an antigen, and separating the serum from this blood using known methods. As polyclonal antibodies, the serum containing polyclonal antibodies may be used. According to needs, a fraction containing polyclonal antibodies can be further isolated from this serum. Alternatively, a monoclonal antibody can be obtained by isolating immune cells from mammals sensitized with an antigen; fusing these cells with myeloma cells, and such; cloning hybridomas thus obtained; and collecting the antibody from the culture as the monoclonal antibody.

To detect the "2090-05" protein, these antibodies may be appropriately labeled. Alternatively, instead of labeling the antibodies, a substance that specifically binds to antibodies, for example, protein A or protein G, may be labeled to arrange an indirect detection of the proteins. More specifically, one example of an indirect detection method is ELISA.

A protein or partial peptides thereof that is used as an antigen may be obtained, for example, by inserting a gene or portion thereof into an expression vector, introducing it into an appropriate host cell to produce a transformant, culturing the transformant to express the recombinant protein, and purifying the expressed recombinant protein from the culture or the culture supernatant. Alternatively, oligonucleotides consisting of the amino acid sequence encoded by the gene, or partial amino acid sequences of the amino acid sequence encoded by the full-length cDNA obtained based on SEQ ID NO: 1 are chemically synthesized to be used as the antigen.

In this invention, eosinophil cells of a test subject are used as the sample. Eosinophil cells can be prepared by a conventional method from the peripheral blood. Specifically, leukocytes are isolated, for example, by fractionating heparinized blood by centrifugation. Next, granulocytes are fractionated, for example, by Ficoll centrifugation of leukocytes, and furthermore eosinophil cells can be isolated, for example, by depletion of neutrophils using the CD16 antibody. A sample for immunological assays of the aforementioned protein can be obtained by disrupting the isolated eosinophils to produce a lysate. Alternatively, a sample for measuring mRNA corresponding to the aforementioned gene can be obtained by extracting mRNA from this lysate. The use of a commercially available kit is convenient for extracting mRNA and preparing a lysate of eosinophils.

Alternatively, the expression level of the gene that serves as the indicator in this invention may be measured not in isolated in eosinophils, but in the whole blood, and peripheral blood leukocyte population. In this case, by correcting the measured values, the change of gene expression levels in cells can be determined. For example, based on the measured value of the expression level of a gene (housekeeping gene), whose expression level is eosinophil specific and is not widely altered regardless of the cellular conditions, the measured value of the expression level of the gene serving as an indicator in this invention can be corrected.

Alternatively, in the case where the protein to be detected is a secretory protein, comparison of the expression level of a gene encoding the protein is accomplished by measuring the amount of the target protein contained in body fluid sample, such as blood and serum, in a subject.

When the result of the test for an allergic disease of this invention shows the elevated expression level of the gene of this invention especially in a patient with an allergic disease such as atopic dermatitis, allergic symptoms are presumed to be improving.

Furthermore, this invention relates to an allergic disease model animal, wherein said animal is a transgenic non-human animal showing the decreased expression level of the polynucleotide of any one of (a) to (d) in eosinophil cells:

(a) A polynucleotide comprising a coding region of the nucleotide sequence of SEQ ID NO: 1;

(b) A polynucleotide encoding a protein comprising the amino acid sequence of SEQ ID NO: 2;

(c) A polynucleotide encoding a protein that is functionally equivalent to a protein that shows increased expression in eosinophils in the remission stage of atopic dermatitis, and comprising an amino acid sequence of SEQ ID NO: 2 in which one or more amino acids have been substituted, deleted, inserted, and/or added; and (d) A polynucleotide encoding a protein that shows increased expression in eosinophils in the remission stage of atopic dermatitis, wherein the polynucleotide hybridizes under stringent conditions with a DNA comprising the nucleotide sequence of SEQ ID NO: 1.

In this invention, decrease in expression level includes a knockout condition in which the function of the gene has been substantially made to disappear. In this invention, the condition in which the function of the gene has virtually disappeared refers to a condition in which neither expression of the gene nor the activity of the protein encoded by this gene is observed. The expression level of the gene can be confirmed by quantitative PCR such as those shown in Examples. Furthermore, that substantially no activity of the translation product protein is detected can be confirmed by comparison to a normal condition.

Such a transgenic animal includes animals that are incapable of expressing the intact activity of the protein, for example, due to artificial mutation of the amino acid sequence and introduction of a stop codon by introducing a mutation into the coding region of the gene. Examples of mutation in the amino acid sequence are substitution, deletion, insertion, and addition of amino acid(s). In addition, by mutagenizing the transcriptional regulatory region of the gene, the expression itself of the gene of this invention can be controlled.

Methods for obtaining transgenic animals with a particular gene as a target are known. That is, a transgenic animal can be obtained by a method where the gene and ovum are mixed and treated with calcium phosphate; a method where the gene is introduced directly into the nucleus of oocyte in pronuclei with a micropipette under a phase contrast microscope (microinjection method, U.S. Pat. No. 4,873,191); or a method where embryonic stem cells (ES cells) are used. Furthermore, there have been developed a method for infecting ovum with a gene-inserted retrovirus vector, a sperm vector method for transducing a gene into ovum via sperm, or such. Sperm vector method is a gene recombination technique for introducing a foreign gene by fertilizing ovum with sperm after a foreign gene has been incorporated into sperm by the adhesion or electroporation method, and so on (M. Lavitranoet, et al. Cell, 57, 717, 1989).

Transgenic animals of the present invention can be produced using all the vertebrates except for humans. More specifically, transgenic animals having various transgene and being modified gene expression levels thereof are produced using vertebrates such as mice, rats, rabbits, miniature pigs, goats, sheep, or cattle.

Transgenic animals of this invention include a knockout animal, in which expression of a homologue of a human gene having the nucleotide sequence of SEQ ID NO: 1 in this animal species is inhibited. Observation of the phenotype of the knockout animal specifically tells the function of the gene that was knocked out. A gene comprising the nucleotide sequence of SEQ ID NO: 1 shows increased expression in eosinophils in the remission stage of atopic dermatitis in humans. Therefore, the animal in which that a homologue of this gene is knocked out is useful as an animal model for allergic diseases.

For example, if the knockout animal of this invention develops dermatitis, or indicates change in measured values relating to some sort of allergic diseases, a screening system to search for a compound having the function to allow recovery therefrom can be constructed. In this case, the thus screened pharmaceutical agent acts on a gene product relating to the severity of an allergic disease, which gene is different from the 2090-05 gene.

A method of producing a knockout animal is well known. For example, the method of producing a knockout mouse by performing homologous recombination using embryonic stem cells, and selecting the embryonic stem cells in which one of the alleles is modified or destroyed, is known. More specifically, a chimeric animal containing cells derived from an embryonic stem cell and cells derived from an embryo, is obtained, for example, by inserting a genetically manipulated embryonic stem cell into a fertilized egg. When this chimeric animal (chimera refers to a single individual formed from somatic cells derived from two or more fertilized eggs) is crossed with a normal mouse, a heterozygote in which one of the alleles is modified or destroyed in its entirety can be produced. Furthermore, a homozygote can be produced by crossing heterozygotes. The transgenic animals of this invention include both the heterozygote and the homozygote.

Homologous recombination refers to a mechanism of genetic recombination that occurs between two genes having the same or very similar nucleotide sequences. PCR can be used to select cells that have undergone homologous recombination. PCR using a portion of an insert gene and a portion of the region in which insertion is expected as primers, can confirm the occurrence of homologous recombination in cells that produce amplification products. Furthermore, when inducing homologous recombination of a gene expressed in an embryonic stem cell, neomycin resistance gene is linked to a transgene and the gene is introduced into a cell to make the cell neomycin resistant, to thereby easily select the cells. This and other known methods and modified methods thereof can be used.

The transgenic animals of this invention are useful for elucidating the mechanism of allergic diseases, and also for testing the safety of the screened compound.

This invention showed that the expression level of the gene, "2090-05", rises in the eosinophils of atopic dermatitis patients in the remission stage. Therefore, an animal in which the expression level of this gene or genes functionally equivalent thereto in eosinophil cells is artificially lowered can be used as an allergic disease model animal. Decrease of the expression level in the eosinophils includes decrease in the expression level of the gene in the entire population of leukocytes. In other words, this phrase includes the decreased expression level of the gene not only in eosinophils alone but also in the entire population of leukocytes. In the present invention, a functionally equivalent gene refers to a gene of any one of the (a) to (d). For example, the aforementioned transgenic animal may be used as the animal model of this invention.

Furthermore, this invention relates to a method of detecting an influence of a candidate compound on the expression level of the polynucleotide of this invention. In this invention, the "2090-05" gene shows a significant increase of the expression level in the eosinophils of atopic dermatitis patients in the remission stage. Therefore, based on the method of detecting an influence on the expression level of the gene, a therapeutic agent for an allergic disease can be obtained by selecting a compound that can increase the expression level of the gene. In the present invention, a compound that increases the expression level of the gene is a compound having the effect of inducing any one of the steps of transcription of the gene, translation, and expression of protein activity.

The method of detecting an influence of a candidate compound on the expression level of the polynucleotide of this invention can be performed in vivo or in vitro. In order to detect an influence in vivo, an appropriate test animal is used. For example, laboratory animals and animal models for an allergic disease that can express the indicator gene, can be used as the test animal. Detection of an influence on the expression level in vivo based on the present invention can be performed, for example, by the steps of:
(1) administering a candidate compound to a test animal; and
(2) measuring the expression level of a polynucleotide of any one of the aforementioned (a) to (d) in eosinophil cells of the test animal.

An influence of a candidate compound for a pharmaceutical agent on the expression level of the 2090-05 gene can be detected by administering the candidate compound for a pharmaceutical agent to the test animal as described above and monitoring the effect of the compound towards expression of the 2090-05 gene in eosinophils of the test animal. Furthermore, a candidate compound for a pharmaceutical agent can be screened by selecting a candidate compound for a pharmaceutical agent that increases the expression level of the 2090-05 gene based on the detection results.

Such screening allows selection of drugs that are involved in various ways in the expression of the 2090-05 gene. Specifically, for example, a candidate compound for a pharmaceutical agent having the following action can be discovered:
Activation of a signal transduction pathway that causes expression of the 2090-05 gene;
Increase of transcription activity of the 2090-05 gene; and
Inhibition of degradation or stabilization of the transcription product of the 2090-05 gene.

An in vitro detection can be performed, for example, by a method where a candidate compound is contacted with cells expressing a gene according to any one of above-descried (a) through (d) to detect expression levels of these genes. More specifically, the method may be carried out according to the following steps of:
(1) contacting a candidate compound with cells that express the polynucleotide according to any one of above-described (a) through (d); and
(2) measuring the expression level of a polynucleotide according to any one of above-described (a) through (d).

In this invention, cells to be used in the step (1) can be obtained by inserting these polynucleotides into an appropriate expression vector and then transfecting suitable host cells with the vector. Any vectors and host cells may be used as long as they are capable of expressing the gene of this invention. Examples of host cells in the host-vector system are *Escherichia coli* cells, yeast cells, insect cells, animal cells, and available vectors usable for each can be selected.

Vectors may be transfected into the host by biological methods, physical methods, chemical methods, and so on. Examples of the biological methods include methods using virus vectors; methods using specific receptors; and the cell-fusion method (HVJ (Sendai virus) method, the polyethyleneglycol (PEG) method, the electric cell fusion method, and microcell fusion method (chromosome transfer)). Examples of the physical methods include the microinjection method, the electroporation method, and the method using gene particle gun. The chemical methods are exemplified by the calcium phosphate precipitation method, the liposome method, the DEAE-dextran method, the protoplast method, the erythrocyte ghost method, the erythrocyte membrane ghost method, and the microcapsule method.

In the detection method of this invention, leukocyte cell lines can be used as cells for expressing the polynucleotide of the aforementioned (a) or (b). Examples of leukocyte cell lines are cell lines derived from leukocytes, such as Eol, YY-1, HL-60, TF-1, and AML14.3D10. Among the leukocyte cell lines, cell lines derived from eosinophils are preferred for the detection method of this invention. The following are cell lines derived from eosinophils:
Eol
YY-1
AML14.3D10

Eol (Eol-1: Saito H et al., Establishment and characterization of a new human eosinophilic leukemia cell line. Blood 66, 1233–1240, 1985) can be obtained from Hayashibara Research Institute. Similarly, YY-1 (Ogata N et al., The activation of the JAK2/STAT5 pathway is commonly involved in signaling through the human IL-5 receptor. Int. Arch. Allergy Immunol., Suppl 1, 24–27, 1997) is available from The Institute of Cytosignal Research. Furthermore, AML14.3D10 (Baumann M A et al., The AML14 and AML14.3D10 cell lines: a long-overdue model for the study of eosinophils and more. Stem Cells, 16, 16–24, 1998) is commercially available from Paul CC at Research Service, VA Medical Center, Dayton, Ohio, USA.

In addition, by culturing for about 1 week in the presence of butyric acid, HL-60 clone 15 (ATCC CRL-1964), which is an undifferentiated leukocyte cell line, can differentiate into eosinophils to give an eosinophil cell line. Eosinophils can be detected due to their morphological characteristic of being polymorphonuclear and having eosinophilic granules. Morphological observations are performed by Giemsa staining and Difquick staining. Generally, human leukocyte cell line including eosinophils can be established by cloning immortalized cells from a leukemia patient sample. Therefore, those skilled in the art can obtain eosinophil cell lines by a conventional method when necessary.

The method of screening first involves contacting a candidate compound with the aforementioned leukocyte cell line. Then, the expression levels of the polynucleotides of (a) or (b) in the leukocyte cell line are measured and a compound that increases the expression level of the gene is selected.

Transformed cells in which expression of the polynucleotide of any one of the aforementioned (a) to (d) is modified can be used as cells for the in vitro detection method. Examples of such transformed cells are cells transformed with an expression vector for an antisense of the polynucleotide. The cell transformed with an antisense expression vector can be obtained according to a principle similar to that for the production of the aforementioned transgenic animal. Using the obtained transformed cell, an influence of the candidate compound on the expression level of the gene can be detected.

In the method of the present invention, expression levels of polynucleotides according to any one of above-described (a) through (d) can be compared by detecting the expression levels of not only proteins encoded by these genes but also the corresponding mRNAs. For the comparison of the expression level using mRNA, the step of preparing mRNA sample as described above is conducted in place of the step of preparing a protein sample. Detection of mRNA and protein can be carried out according to the known methods as described above.

Furthermore, based on the disclosure of this invention, it is possible to obtain the transcriptional regulatory region of the gene of the present invention and to construct a reporter assay system. Reporter assay system means an assay system of screening for a transcriptional regulatory factor that acts on the transcriptional regulatory region by using the expression level of a reporter gene that is located downstream of the transcriptional regulatory region and expressed under the control of the regulatory region as an indicator.

More specifically, this invention relates to a method of screening for therapeutic agents for an allergic disease, the method comprising the steps of:
(1) contacting a candidate compound with a cell transfected with a vector containing the transcription regulatory region of an indicator gene and a reporter gene that is expressed under the control of this transcription regulatory region;
(2) measuring the activity of the reporter gene; and
(3) selecting a compound that increases the expression level of the reporter gene compared to a control,
wherein the indicator gene is a gene selected from the group consisting of "2090-05" and genes functionally equivalent thereto.

A transcriptional regulatory region is exemplified by promoter, enhancer, as well as CAAT box, and TATA box, which are usually found in the promoter region. Examples of the reporter gene include the chloramphenicol acetyltransferase (CAT) gene, the luciferase gene, and growth hormone genes.

A transcriptional regulatory region of the gene of the present invention can be obtained as follows. Specifically, first, based on the nucleotide sequence of a cDNA disclosed in this invention, a human genomic DNA library, such as BAC library and YAC library, is screened by a method using PCR or hybridization to obtain a genomic DNA clone containing the sequence of the cDNA. Based on the sequence of the resulting genomic DNA, the transcriptional regulatory region of a cDNA disclosed in this invention is predicted and obtained. The obtained transcriptional regulatory region is cloned so as to be localized upstream of a reporter gene to prepare a reporter construct. The resulting reporter construct is introduced into a cultured cell strain to prepare a transformant for screening. By contacting a candidate compound with this transformant to detect the expression of a reporter gene, it is possible to assess the effect of the candidate compound on the transcriptional regulatory region.

Based on the method of detecting the effect on the expression level of the polynucleotides of this invention, it is possible to carry out screening for a compound that alters the expression level of the polynucleotides. This invention relates to a method of screening for a compound that alters the expression level of a polynucleotide according to any one of above-described (a) through (d), comprising following steps.

That is, the present invention relates to a method of screening for a compound that raises the expression level of a polynucleotide of any one of above-described (a) through (d), the method comprising the steps of detecting the effect of a candidate compound on the expression level of the polynucleotide in vivo and/or in vitro, and selecting a compound that raises the expression level compared to a control.

Alternatively, this invention relates to a method of screening for a compound that acts on the transcriptional regulatory region by the reporter assay utilizing the transcriptional regulatory region of the gene having the nucleotide sequence of SEQ ID NO: 1. Based on the results of reporter assay according to this invention, by selecting a compound that raises the expression level of the reporter gene compared to a control, it is possible to obtain a compound that induces the expression of the gene having the nucleotide sequence of SEQ ID NO: 1.

The polynucleotide, antibody, cell line, or model animal, which are necessary for the various methods of screening of this invention, can be combined in advance to produce a kit. More specifically, such a kit may comprise, for example, a cell that expresses the indicator gene, and a reagent for measuring the expression level of the indicator gene. As a reagent for measuring the expression level of the indicator gene, for example, an oligonucleotide that has at least 15 nucleotides complementary to the polynucleotide comprising the nucleotide sequence of at least one indicator gene or to the complementary strand thereof is used. Alternatively, an antibody that recognizes a peptide comprising amino acid sequence of at least one indicator protein may be used as a reagent. In these kits may be packaged a substrate compound used for the detection of the indicator, medium and a vessel for cell culturing, positive and negative standard samples, and furthermore, a manual describing how to use the kit. A kit of this invention for detecting the effect of a candidate compound on the expression level of the 2090-05 gene can be used as a kit for screening for a compound that modifies the expression level of the 2090-05 gene.

Test candidate compounds used in these methods include, in addition to compound preparations synthesized by known chemical methods, such as steroid derivatives and compound preparations synthesized by combinatorial chemistry, and mixtures of multiple compounds such as extracts from animal or plant tissues, or microbial cultures and their purified preparations.

Compounds selected by the screening method of this invention are useful as the therapeutic agent for an allergic disease. A therapeutic agent for allergic diseases of the present invention can be formulated by including a compound selected by the screening methods as the effective ingredient, and mixing with a physiologically acceptable carrier, excipient, diluent, and such. To ameliorate allergic symptoms, the therapeutic agent for allergic diseases of this invention can be administered orally or parenterally.

Oral drugs can take any dosage forms selected from granules, powder, tablets, capsules, solution, emulsion, suspension, and so on. Injections can include subcutaneous injection, intramuscular injection, and intraperitoneal injection.

Although the dosage may vary depending on the age, sex, body weight, and symptoms of a patient; treatment effects; method for administration; treatment duration; type of active ingredient contained in the drug composition; and such, a range of 0.1 to 500 mg, preferably 0.5 to 20 mg per dose for an adult can be administered. However, the dose changes according to various conditions, and thus in some case a more smaller amount than that mentioned above is sufficient whereas an amount above the above-mentioned range is required in other cases.

BEST MODE FOR CARRYING OUT THE INVENTION

Figure 1:
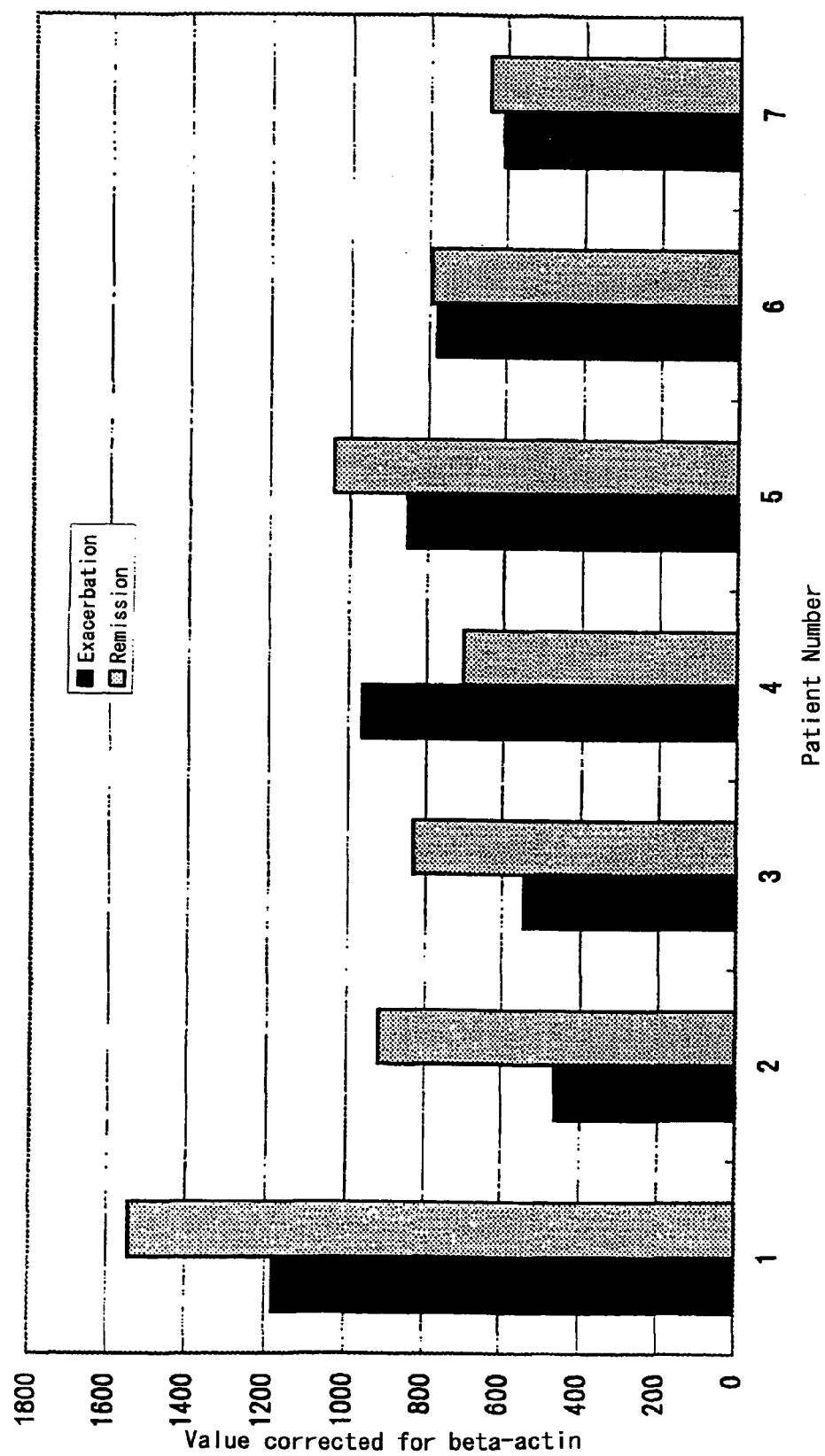
FIG. 1 shows the 2090-05 gene expression level (copy/ng RNA) which is corrected for β-actin, in the exacerbation stage and in the remission stage of atopic dermatitis patients (patient numbers 1 to 7).

The present invention will be explained in detail below with reference to examples, but it is not to be construed as being limited thereto.

EXAMPLE 1

Differential Display Analysis

Screening was performed in order to find novel therapy related genes or genes useful for diagnosis, whose expression in hemocytes isolated from the peripheral blood of an atopic dermatitis patient in the exacerbation stage differs from that in the stage of remission due to drug therapy and such.

(1) Test Subject

Table 1 shows the profiles of seven atopic dermatitis patients whose blood samples were drawn. Allergen nonspecific (Total IgE), mite-specific, and cedar-specific IgEs were measured by the EIA method. More specifically, the test sera were allowed to react to an anti-human IgE antibody-bound cap to bind thereto allergen non-specific IgE antibody or mite- or cedar-specific IgE antibodies in the sera. Next, β-D-galactosidase-labeled anti-human IgE antibody and a substrate solution (4-methylumbelliferyl-β-D-galactopyranoside) were added and allowed to react to produce a fluorescent substance. The reaction was quenched by adding a quenching solution, and the antibody concentration was determined from the fluorescence intensity of a simultaneously measured standard IgE. LDH was measured by the UV method (Wroblewski-La Due method) and the rate of decrease of NADH caused by the reaction of pyruvic acid with NADH is calculated from decrease in absorbance. L-type Wako LDH (Wako Pure Chemicals) and 7170-type automatic analyzer (Hitachi) were used for measuring the LDH values. The number of eosinophils was measured by microscopic examination and automatic hemocyte analyzer SE-9000 (RF/DC impedance system, Sysmex) using 2 ml of EDTA-added blood as the sample.

TABLE 1

| | Patient number | | | | | | | | | | | | | |
|---|---|---|---|---|---|---|---|---|---|---|---|---|---|---|
| | 1 | | 2 | | 3 | | 4 | | 5 | | 6 | | 7 | |
| | Donor ID | | | | | | | | | | | | | |
| | PA00002 | | PA00068 | | PA00069 | | PA00070 | | PA00071 | | PA00073 | | PA00164 | |
| | Condition | | | | | | | | | | | | | |
| | Exacerbation stage | Remission stage | Exacerbation stage | Remission stage | Exacerbation stage | Remission stage | Exacerbation stage | Remission stage | Exacerbation stage | Remission stage | Exacerbation stage | Remission stage | Exacerbation stage | Remission stage |
| T-IgE | 6100 | 7100 | 2600 | 2100 | 13000 | 20000 | 15000 | 15000 | 9300 | 9200 | 17000 | 8800 | 2100 | 1600 |
| Mite | 82.1 | 73.8 | 66.4 | >100 | 72.2 | 66.7 | 85.9 | 90.9 | 74.6 | 70.8 | 88 | >100 | >100 | 82.8 |
| Cedar | 57.1 | 77.2 | 14.4 | 19.7 | 15.2 | 22.5 | 61.9 | 59.6 | 64.2 | 71.1 | 18.3 | 9.27 | 6.51 | 3.61 |
| LDH | 910 | 475 | 293 | 296 | 398 | 250 | 173 | 182 | 534 | 297 | 620 | 598 | 343 | 393 |
| Eosinophil (%) | 16 | 11.7 | 23.2 | 10.1 | 16 | 6.2 | 8.6 | 12.1 | 28.2 | 13.4 | 13.4 | 12.3 | 12.9 | 10.6 |
| Eosinophil (/mm³) | 1620 | 611 | 1420 | 468 | 2070 | 527 | 738 | 752 | 1830 | 972 | 945 | 846 | 898 | 847 |
| Internal use | ALDECIN inhalant, Theodir INTAL inhalant, ZADITEN | | ZADITEN | | | | ZADITEN, Shofusan ATARAX P | | CELTECT INTAL oral preparation | | ZADITEN DS | INTAL →none | PREDONINE (only 181) Theolong, ALDECIN | |
| External use | Body: Zalucs Face: LOCOID | | Body: LOCOID Face: nonsteroid | | Body: Zalucs Face: nonsteroid | | Body: LOCOID Face: nonsteroid | | Body: LOCOID Face: nonsteroid | | Body: Zalucs→ RINDERON V Face: LOCOID | | Body: Zalucs Face: LOCOID | |
| Other diseases | Asthma (moderate) | | | | | | | | Asthma (moderate) | | | | Asthma (severe/mild) | |

(2) Differential Display Analysis

A 3% dextran solution was added to whole blood drawn from a patient, and this was left to stand at room temperature for 30 minutes to precipitate erythrocytes. The upper layer leukocyte fraction was collected, layered on top of Ficoll solution (Ficoll-Paque PLUS; Amersham Pharmacia Biotech), and centrifuged at 1500 rpm for 30 minutes at room temperature. The granulocyte fraction that collected in the lower layer was reacted with CD16 antibody magnetic beads at 4° C. for 30 minutes, and cells that had eluted without being trapped in the separation using MACS were used in the experiment as eosinophils.

Eosinophils prepared as described above were dissolved in Isogen (Nippon Gene; Wako Pure Chemicals), and from this solution, RNA was separated according to the protocol attached to Isogen. Chloroform was added, the mixture was stirred and centrifuged, and the aqueous layer was collected. Next, isopropanol was added, the mixture was stirred and centrifuged, and the precipitated total RNA was collected. DNase (Nippon Gene; Wako Pure Chemicals) was added to the collected total RNA, the mixture was reacted at 37° C. for 15 minutes, and RNA was collected by phenol-chloroform extraction followed by ethanol precipitation.

Fluorescent Differential Display (abbreviated to DD) analysis using total RNA thus prepared was carried out according to the literature (T. Ito et al., 1994, FEBS Lett. 351: 231–236). The total RNA was reverse transcribed to obtain cDNA. In the first DD-PCR, 0.2 μg each of total RNA was used for three types of anchor primers to synthesize cDNAs. In the second DD-PCR, 0.4 μg each of total RNA was used for the synthesis of cDNAs using three types of anchor primers. In both cases, the cDNAs were diluted to a final concentration equivalent to 0.4 ng/μl RNA and used for further experiments. The DD-PCR was carried out using an amount of cDNA equivalent to 1 ng RNA per reaction. The reaction mixture composition is shown in Table 2.

TABLE 2

| | |
|---|---|
| cDNA (equivalent to 0.4 ng/μl RNA) | 2.5 μl |
| Arbitrary primer (2 μM) | 2.5 μl |
| 10x AmpliTaq PCR buffer | 1.0 μl |
| 2.5 mM dNTP | 0.8 μl |
| 50 μM anchor primer (GT15A, GT15C, or GT15G) | 0.1 μl |
| Gene Taq (5 U/μl) | 0.05 μl |
| AmpliTaq (5 U/μl) | 0.05 μl |
| dH$_2$O | 3.0 μl |
| Total volume | 10.0 μl |

The PCR was carried out at following condition: 1 cycle of "95° C. for 3 min, 40° C. for 5 min, and 72° C. for 5 min"; subsequently 30 cycles of "94° C. for 15 sec, 40° C. for 2 min, and 72° C. for 1 min"; after these cycles, 72° C. for 5 min; and then continuously 4° C.

Reactions were conducted using 287 primer pairs: i.e., anchor primers GT15A (SEQ ID NO: 3), GT15C (SEQ ID NO: 4), and GT15G (SEQ ID NO: 5) were used in combination with arbitrary primers AG 1 to AG 110, AG 111 to AG 199, and AG 200 to AG 287, respectively. As for the arbitrary primers, oligomers having 10 nucleotides with a GC content of 50% were designed and synthesized.

For gel electrophoresis, a 6% denaturing polyacrylamide gel was prepared, and 2.5 μl sample from the PCR was applied and run under 40 W for 210 min. After electrophoresis, the gel was scanned by Hitachi fluorescence imaging analyzer FMBIO II, and the gel image was obtained by detecting fluorescence.

Samples from both the exacerbation stage and the remission stage were phoresed side by side. Gene bands shifted in the same direction in most patients, showing altered expressions, were visually determined, excised, and subjected to TA cloning and sequence determination. As a result, an eosinophil gene (DD analysis band ID 2090-05; hereinafter this gene is referred to as "2090-05") whose expression is significantly enhanced in the remission stage than in the exacerbation stage was identified. The primer set used for amplifying band ID 2090-05 is shown below. Furthermore, the nucleotide sequence of the DD band of 2090-05 is shown in SEQ ID NO: 15.

Band ID: 2090-05
Length of fragment: 430 bp (excluding the nucleotide sequence of the primer)
Anchor primer: GT15A
Name of arbitrary primer: AG00055
Sequence of arbitrary primer: CCGTGAATTC (SEQ ID NO: 6)

(3) Expression Analysis

In order to confirm the expression level of the 2090-05 gene quantitatively, quantitative PCR was further performed by ABI 7700 using the same clinical sample. Primers and TaqMan probe used for measurement by ABI 7700 were designed using Primer Express (PE Biosystems) from the sequence information obtained by the differential display method. The 5'-end and the 3'-end of TaqMan probe were labeled with FAM (6-carboxy-fluorescein) and TAMRA (6-carboxy-N,N,N',N'-tetramethylrhodamine), respectively.

```
2090-05 forward primer (SEQ ID NO: 7)
GGTCGATTCTGTGTGTGGATGATAG 2090-05 reverse primer (SEQ ID NO: 8)
GAGTTGATGCACTGCGACTTAA 2090-05 TaqMan probe (SEQ ID NO: 9)
TGATGTCAGTTTCTCAACGCAGCCA
``` cDNA was used as a template which was prepared by reverse transcription from the total RNA using poly-T (12 to 18 mer) as primers. In order to make a standard curve for the calculation of copy numbers, a plasmid clone containing the nucleotide sequence amplified using both primers was prepared, and serial dilutions thereof were utilized as the template for the reaction. The reaction mixture composition for monitoring PCR amplification is shown in Table 3.

TABLE 3

Reaction mixture composition for ABI-PRISM 7700 (amount per well)

| | |
|---|---|
| Sterile distilled water | 25.66 (μl) |
| 10x TaqMan buffer A | 5 |
| 25 mM MgCl$_2$ | 7 |
| dATP (10 mM) | 1.2 |
| dCTP (10 mM) | 1.2 |
| dGTP (10 mM) | 1.2 |
| dUTP (10 mM) | 1.2 |
| Forward Primer (100 μM) | 0.15 |
| Reverse Primer (100 μM) | 0.15 |
| TaqMan Probe (6.7 μM) | 1.49 |
| AmpliTaq Gold (5 U/μl) | 0.25 |
| AmpErase UNG (1 U/μl) | 0.5 |
| Template solution | 5 |
| Total volume | 50 |

In order to correct the difference in the cDNA concentrations between the samples, the same quantitative analysis was carried out for the β-actin gene that was used as internal standard, and, by performing correction based on its copy number, the copy number of the target gene was calculated. For the quantification of the β-actin gene, the human cDNA was used as a template.

As the primers and probe for the measurement of β-actin were used those attached to TaqMan β-actin Control Reagents (PE Biosystems) Their nucleotide sequences are as shown below. The "2090-05" gene expression levels (copy/ng RNA) corrected for that of β-actin are shown in Table 4 and FIG. 1.

β-Actin forward primer (SEQ ID NO: 10)
TCA CCC ACA CTG TGC CCA TCT ACG A

β-Actin reverse primer (SEQ ID NO: 11)
CAG CGG AAC CGC TCA TTG CCA ATG G

β-actin TaqMan probe (SEQ ID NO: 12)
5'-(FAM)ATGCCC-T(TAMRA)-CCCCCATGCCATCCTGCGTp-3'

FAM: 6-carboxy-fluorescein
TAMRA: 6-carboxy-N,N,N',N'-tetramethylrhodamine

TABLE 4

2090-05 gene expression level (copy/ng RNA)

| Patient No. | Exacerbation stage | Remission stage |
| --- | --- | --- |
| 1 | 1180.75 | 1545.49 |
| 2 | 462.7 | 919.6 |
| 3 | 543.88 | 831.07 |
| 4 | 853.14 | 1040.26 |
| 6 | 780.6 | 794.44 |
| 7 | 607.18 | 645.45 |

(4) Statistical Analysis

Using the above-mentioned data, parametric multiple comparison test and non-parametric multiple comparison test were carried out. Statistical analysis was carried out using SAS Pre-clinical Package of The SAS SYSTEM, Version 4.0 (SAS Institute Inc.). The results are shown in Table 5.

TABLE 5

| Test between two corresponding groups | | t-Test between two |
| --- | --- | --- |
| t-Test Parametric | Wilcoxon test Non-parametric | corresponding groups of atopic dermatitis patients (n = 7) |
| E < R p = 0.144 | E < R p = 0.1094 | E < R p = 0.011 |

As a result, among the seven atopic dermatitis patients mentioned above, increase in the 2090-05 gene expression was observed in six patients, excluding patient number 4. The change in expression levels of the 2090-05 gene in the samples of these seven patients (n=7) was then analyzed statistically. Statistical analysis was carried out using SAS Pre-clinical Package of The SAS SYSTEM, Version 4.0 (SAS Institute Inc.).

The statistical analysis confirmed significant increase in expression in the remission stage compared to the exacerbation stage (p=0.011). These findings indicate that expression of this gene is increased in the remission stage of atopic dermatitis. This means that measuring the expression of this gene has a diagnostic value in atopic dermatitis. This eosinophil-derived gene is medically useful as a therapeutic target or a diagnostic marker for atopic dermatitis.

EXAMPLE 2

Expression of 2090-05 Gene in Various Blood Cells 2090-05 gene expression was examined in cells separated from peripheral blood collected from five normal healthy subjects. Separation of eosinophils (E) was carried out as described above. After the elution of eosinophils, neutrophils (N) were prepared by releasing the cells, which were trapped with CD16 antibody magnetic beads, from the magnetic field, eluting, and recovering. On the other hand, the monocyte fraction recovered in the middle layer by the Ficoll-centrifugation was separated into the fraction eluted from MACS CD3 antibody magnetic beads (mixture of M (monocyte) and B cell) and fraction trapped therein (T-cell fraction). Then, using MACS CD14 antibody magnetic beads, the eluted fraction was separated into the eluted fraction (B cell fraction) and trapped fraction (monocyte fraction), and those three fractions were referred to as the purified T cells, B cells, and monocytes.

Eosinophils were solubilized using Isogen, while neutrophils, T cells, B cells and monocytes were solubilized with RNeasy (Qiagen), and total RNA were extracted, treated with DNase (by the same methods as described above), and subjected to the gene expression analysis. Primers, probes, and others used were the same as above. Average expression levels (AVERAGE: copy/ng (corrected value)) in these blood cells are shown below.

eosinophil (E): 1454 neutrophil (N): 139 basophil (B): 1056

T-cell (T): 760 monocyte (M): 473

EXAMPLE 3

Elongation of the Nucleotide Sequence

Based on the nucleotide sequence determined in Example 1, the nucleotide sequence of the gene of this invention was analyzed by the 5' RACE method. Marathon cDNA was synthesized using Human Placenta Poly A+ RNA (CLONTECH) according to the protocol of Marathon cDNA Amplification Kit (CLONTECH), and using this as a template, PCR was carried out using the B2090-specific primer, 2090-05F, and AP1 primer included in the kit. Furthermore, using this amplified fragment as a template, PCR was carried out using primer 2090-05F and sequence [AP2] in the adapter. When the amplified fragment was subcloned and the sequence was determined, a sequence of approximately 1.8 kb containing the sequence of c2090-05 was obtained. Similarly, PCR was carried out using the B2090-specific primer, 2090-05R, and AP1 primer included in the kit. Furthermore, using this amplified fragment as a template, PCR was carried out using primer 2090-05R and sequence [AP2] in the adapter. he amplified fragment was subcloned and the sequence was determined to obtain a sequence of 0.7 kb containing the sequence of c2090-05 and having a total length of 2214 bp. This 2214 bp nucleotide sequence was determined, and is shown in SEQ ID NO: 19. In addition, the deduced amino acid sequence based on this nucleotide sequence is shown in SEQ ID NO: 2.

Primer Sequences

```
2090-05F: CATGGTTGAGGGAGACTGTGATG   (SEQ ID NO: 13)

2090-05R: GTGCGACACTCAATGAGACACTG   (SEQ ID NO: 14)
```

EXAMPLE 4

Determination of the Upstream Sequence

ESTs that may become an upstream sequence (EST comprising the nucleotide sequence of SEQ ID NO: 19, and also comprising the 5' side nucleotide sequence), were searched out and based on the ESTs, the following primers were constructed to perform PCR.

Primer Sequences

```
Primer 1F:
ATAACAGAGGTGGCCGCGACCACA       (SEQ ID NO: 15)

Primer 9R:
TTATGTTCCACTTACTGGTTCTGTGAT    (SEQ ID NO: 16)

Primer 7R:
GGAATCCACGGCTAACATGGCTAT       (SEQ ID NO: 17)
```

Fetal liver, lymph node, fetal brain, spleen, thymus, and bone marrow Marathon-Ready DNA (CLONTECH) were used as templates. The first PCR amplification was performed using five of the above-mentioned templates and the enzyme of Expand High Fidelity PCR system (Roche). The reaction mixture composition for the PCR contained 2 µl of ×10 buffer, 2 µl each of 2.5 mM dNTPs, 0.5 pmol each of Primer 1F and Primer 9R as primers, 1 µl of DMSO, and 2 µl of template. The mixture was combined with 0.2 µl of the enzyme and diluted to 20 µl with distilled water. In this system, the reaction was carried out at 94° C. for 5 min, followed by 30 cycles of "94° C. for 30 sec, 55° C. for 30 sec, and 65° C. for 1 min", and then at 72° C. for 7 min. PCR of 25 cycles was carried out similarly using 2 µl of this PCR product, and 0.5 pmol each of Primer 1F and Primer 7R as primers.

As a result, bands of approximately 0.6 kb were found for the fetal liver, lymph node, fetal brain, spleen, and bone marrow samples. The nucleotide sequences of these DNA fragments were determined by conventional methods. The result showed the nucleotide sequence of SEQ ID NO: 1, which corresponds to SEQ ID NO: 19 having approximately 204 additional nucleotides at its upstream (5' side). The newly discovered nucleotide sequence except for SEQ ID NO: 19 in the nucleotide sequence of SEQ ID NO: 1 is as follows:

```
5'-ATAACAGAGGTGGCCGCGACCACAGCCACCCCTGACGGAGGCCCCAG

AGCGACTGCAACAAAAGGAGCCGGGGTACACTCGGGCGAGAGGCCCCCTC

ACTCCCTCTCTAGTAATGCAAGAACTGCGGTCCCCAGCCCGGTGGAGGCA

GCGGCGGCGAGCGATCCCGCGGCGGCCCGCAATGGACTGGCCGAGGGCAC

CGAGCAG-3'
```

EXAMPLE 5

Measurement of the Length of the 2090-05 mRNA in Various Organs

Figure 2:
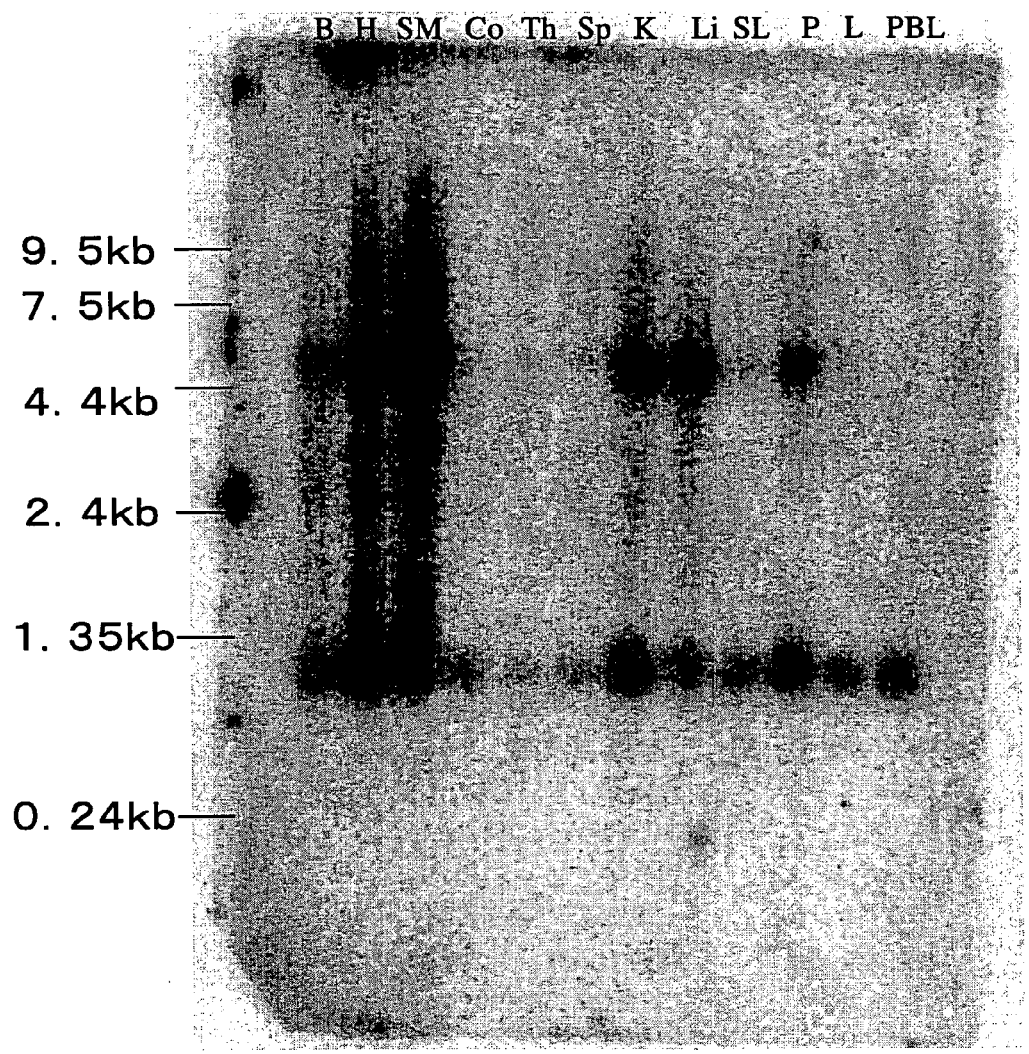
FIG. 2 is a photograph of electrophoretic patterns showing the expression of the 2090-05 gene in various organ as the result of Northern hybridization.

Northern hybridization was carried out using Human 12-Lane MTN Blot (Clontech), which is a membrane onto which mRNAs prepared from various organs (brain, heart, skeletal muscle, large intestine, thymus, spleen, kidney, liver, small intestine, placenta, lung, and peripheral blood leukocytes) have been transferred. PCR amplification was performed using Primer 1F and Primer 9R as a primer set, and fetal liver Marathon-Ready DNA (CLONTECH) as a template, and the obtained DNA fragment was purified using PCR Product Purification Kit (QIAGEN). The purified DNA fragment was labeled with $^{32}$P using Random Primer Labeling Kit (TAKARA), and was then used as a probe. Using Express Hybridization Solution (CLONTECH), Northern hybridization and membrane washing were carried out according to the attached manual. The washed membrane was exposed to an imaging plate to develop the images using Molecular Imager System (BIO-RAD) (FIG. 2). In the tissues used, mRNA of approximately 5.0 kb and approximately 0.8 kb were found to be expressed. The full length of the 2090-05 gene discovered by this invention is expected to be approximately 5.0 kb long.

INDUSTRIAL APPLICABILITY

The present invention provided a gene whose expression level differs between the exacerbation stage and the remission stage of atopic dermatitis patients. The use of the expression of the gene of this invention as an indicator, enables testing for an allergic disease and screening for a candidate compound for a therapeutic agent for the disease.

Expression levels of allergic disease-associated genes provided by the present invention can be easily detected regardless of the types of allergens. Therefore, pathological conditions of allergic diseases can be comprehensively understood.

In addition, using peripheral blood eosinophils as a specimen, the expression level of genes can be analyzed in a much less invasive manner to patients according to the method for testing for allergic diseases of the present invention. Furthermore, according to the gene expression analysis method of the present invention, in contrast to protein measurements such as ECP, highly sensitive measurement with a trace sample can be accomplished. Gene analysis technique trends toward high-throughput and lower prices. Therefore, the test method according to the present invention is expected to become an important bedside diagnostic method in the near future. In this sense, these genes associated with pathological conditions are highly valuable in diagnosis.

The invention claimed is:

1. A method of testing for an allergic disease, said method comprising the steps of:
   a) measuring the expression level of a gene comprising the nucleotide sequence of SEQ ID NO:1 in eosinophil cells of a test subject; and
   b) comparing the measured expression level to the expression level of the gene in eosinophil cells of a healthy subject;
   wherein increased expression of SEQ ID NO:1 is indicative of allergic disease.

2. The testing method of claim 1, wherein the allergic disease is atopic dermatitis.

3. The testing method of claim 1, wherein the expression level of a gene is measured by cDNA PCR.

4. The testing method of claim 1, wherein the expression level of a gene is measured by detecting a protein encoded by the gene.

* * * * *

SEQUENCE LISTING

<160> NUMBER OF SEQ ID NOS: 19

<210> SEQ ID NO 1
<211> LENGTH: 2418
<212> TYPE: DNA
<213> ORGANISM: Homo sapiens

<400> SEQUENCE: 1

| | | | | | |
|---|---|---|---|---|---|
| ataacagagg | tggccgcgac | cacagccacc | cctgacggag | gccccagagc | gactgcaaca | 60 |
| aaaggagccg | gggtacactc | gggcgagagg | ccccctcact | ccctctctag | taatgcaaga | 120 |
| actgcggtcc | ccagcccggt | ggaggcagcg | gcggcgagcg | atcccgcggc | ggcccgcaat | 180 |
| ggactggccg | agggcaccga | gcaggaggag | gaggaggaag | acgagcaggt | gcggctgctg | 240 |
| tcttcgtccc | tgaccgccga | ctgcagctta | agaagcccctt | cgggcaggga | ggttgagcct | 300 |
| ggggaggatc | ggacgatacg | atatgtccga | tatgaatccg | agctacaaat | gcccgatatc | 360 |
| atgagactga | tcaccaaaga | tctgtccgaa | ccctactcca | tttataccta | tagatatttt | 420 |
| atccacaact | ggccacagct | gtgcttcttg | gccatggtag | gggaggagtg | tgtaggtgcc | 480 |
| atcgtttgca | agttggatat | gcacaaaaag | atgttccgca | gaggttatat | agccatgtta | 540 |
| gccgtggatt | ccaaatacag | gagaaatggc | attggtacta | acttggttaa | gaaagctata | 600 |
| tatgccatgg | ttgagggaga | ctgtgatgag | gttgttttgg | aaaccgaaat | aacaaataag | 660 |
| tccgctttga | aactttatga | aaatcttggt | tttgttcgag | ataagaggct | gttcagatac | 720 |
| tatttaaatg | gagttgatgc | actgcgactt | aaactgtggc | tgcgttgaga | aactgacatc | 780 |
| aaggaacaac | tatcatccac | acagaatcga | cctttgcatg | caatgcaatt | tgtacagaat | 840 |
| tgctttgcag | gtggatttag | taatttccat | gcagctctta | cctgtcagtg | tctcattgag | 900 |
| tgtcgcacaa | tatttgttgc | actttggcat | ggcacatttg | ttctgaatta | aaagattgtt | 960 |
| ttaaacttca | ggagttcttt | tggtaccaac | aagatgtgcc | agttgatagc | caagatttat | 1020 |
| gtgttcattt | gcaaagtctg | ctgacaatgt | tatttacaca | gtgatcattt | tatcacagaa | 1080 |
| ccagtaagtg | gaacataatt | tttgtttccc | taaaaagcca | atgtggaatt | gtaaaagtct | 1140 |
| ttaagtatac | taacatttca | cacaaaaacct | gccctagttt | tctgaagtgg | gtgagggaga | 1200 |
| cgcttcagtt | ttaggtttta | ttttttcaat | attaaatttt | ccattcttga | atattggtac | 1260 |
| ctcagtgatt | agtgaatgaa | aaaaatgtag | ggtgggtatg | tcttacaatg | agtaaaggta | 1320 |
| acaattaaat | tttgtctgcc | agtgcctgtg | tagataagta | tatttgtctt | catctccagt | 1380 |
| ttttgaatgc | atgctatctt | ttcctttct | ttaaggcctt | tgcaagcaaa | cttttgtttt | 1440 |
| tatttaaatt | ctaaatttga | taaattattt | cagatttta | taatttggat | acttttttca | 1500 |
| ggtgaatgaa | agaatggttt | acttagaag | tcccttttc | cttacagtaa | caagttgaat | 1560 |
| ctacttggaa | aattgagaaa | tggctcaaaa | gagataagaa | aagttgatgg | agccgggaat | 1620 |
| tgctggggtt | tagatgcact | ttttcttttg | agagtaaggg | aagttttgga | aaagaataga | 1680 |
| aaattagtgt | aagttgatat | gattttattt | aatcaaaatt | actgctacgc | tgcgaagaac | 1740 |
| agcttttaca | aagtagctga | atttgttttt | cccacttgat | ttggattcac | attgctttca | 1800 |
| tttcttaaaa | tgcttcactt | caggttcttg | gtcttggaaa | taaatttcaa | ggtgcattgt | 1860 |
| atccatttta | agctgcttta | ttttattttc | acttgtatga | gcaaattctt | ggggagctt | 1920 |
| tgcttttctt | ctgccagaaa | aacaaaaggg | ggaaatgaaa | atctttttg | gaatgagttc | 1980 |
| tgtgggtttt | cttaacagcc | accatgttta | ttagttacat | tgtgttttgg | ccaatcagtg | 2040 |

-continued

```
caatgtaaca aattttacag ttaattgctt tcaattgagt cagtaaacct gtgatagata    2100
atttatttaa ctggaaaacc taggtaccca taagaaaaaa gattcattct ctgtgaaaac    2160
tgtaggaatc tgttgttgtt ttcatttgaa tatgctctac ttctgctcta gtatttggtt    2220
tggaatatat tttgtggctc taattactgt atttttaaaa aaaccctacc tccattaaca    2280
gttggtaaag gccccttttc aggaaagttt gttgcttttt ttttttttaa aggaaagctg    2340
ctctctgctc agtatagtgt tttgaaagtg aacatagtaa caaatacttt aaaaataaag    2400
atacacaatt tatatttg                                                  2418
```

<210> SEQ ID NO 2
<211> LENGTH: 255
<212> TYPE: PRT
<213> ORGANISM: Homo sapiens

<400> SEQUENCE: 2

```
Ile Thr Glu Val Ala Ala Thr Thr Ala Thr Pro Asp Gly Gly Pro Arg
  1               5                  10                  15

Ala Thr Ala Thr Lys Gly Ala Gly Val His Ser Gly Glu Arg Pro Pro
                 20                  25                  30

His Ser Leu Ser Ser Asn Ala Arg Thr Ala Val Pro Ser Pro Val Glu
             35                  40                  45

Ala Ala Ala Ala Ser Asp Pro Ala Ala Ala Arg Asn Gly Leu Ala Glu
         50                  55                  60

Gly Thr Glu Gln Glu Glu Glu Glu Asp Glu Gln Val Arg Leu Leu
 65                  70                  75                  80

Ser Ser Ser Leu Thr Ala Asp Cys Ser Leu Arg Ser Pro Ser Gly Arg
                 85                  90                  95

Glu Val Glu Pro Gly Glu Asp Arg Thr Ile Arg Tyr Val Arg Tyr Glu
                100                 105                 110

Ser Glu Leu Gln Met Pro Asp Ile Met Arg Leu Ile Thr Lys Asp Leu
            115                 120                 125

Ser Glu Pro Tyr Ser Ile Tyr Thr Tyr Arg Tyr Phe Ile His Asn Trp
        130                 135                 140

Pro Gln Leu Cys Phe Leu Ala Met Val Gly Glu Cys Val Gly Ala
145                 150                 155                 160

Ile Val Cys Lys Leu Asp Met His Lys Lys Met Phe Arg Arg Gly Tyr
                165                 170                 175

Ile Ala Met Leu Ala Val Asp Ser Lys Tyr Arg Arg Asn Gly Ile Gly
            180                 185                 190

Thr Asn Leu Val Lys Lys Ala Ile Tyr Ala Met Val Glu Gly Asp Cys
        195                 200                 205

Asp Glu Val Val Leu Glu Thr Glu Ile Thr Asn Lys Ser Ala Leu Lys
    210                 215                 220

Leu Tyr Glu Asn Leu Gly Phe Val Arg Asp Lys Arg Leu Phe Arg Tyr
225                 230                 235                 240

Tyr Leu Asn Gly Val Asp Ala Leu Arg Leu Lys Leu Trp Leu Arg
                245                 250                 255
```

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 3 gtttttttttt tttttta                                                17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 4 gtttttttttt tttttc                                                 17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 5 gtttttttttt tttttg                                                 17

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 6
ccgtgaattc                                                         10

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 7
ggtcgattct gtgtgtggat gatag                                        25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 8
gagttgatgc actgcgactt aa                                           22

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized probe sequence

```
<400> SEQUENCE: 9
tgatgtcagt ttctcaacgc agcca                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
tcacccacac tgtgcccatc tacga                                          25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11
cagcggaacc gctcattgcc aatgg                                          25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:an
      artificially synthesized probe sequence
<220> FEATURE:
<221> NAME/KEY: misc_binding
<222> LOCATION: (7)
<223> OTHER INFORMATION: Label TAMRA

<400> SEQUENCE: 12
atgccctccc ccatgccatc ctgcgt                                         26

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13
catggttgag ggagactgtg atg                                            23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 14
gtgcgacact caatgagaca ctg                                            23

<210> SEQ ID NO 15
<211> LENGTH: 410
<212> TYPE: DNA
<213> ORGANISM: Homo sapiens
```

```
<400> SEQUENCE: 15
aaacaatctt ttaattcaga acaaatgtgc catgccaaag tgcaacaaat attgtgcgac      60
actcaatgag acactgacag gtaagagctg catggaaatt actaaatcca cctgcaaagc    120
aattctgtac aaattgcatt gcatgcaaag gtcgattctg tgtggatgat agttgttcct    180
tgatgtcagt ttctcaacgc agccacagtt taagtcgcag tgcatcaact ccatttaaat    240
agtatctgaa cagcctctta tctcgaacaa aaccaagatt ttcataaagt ttcaaagcgg    300
acttatttgt tatttcggat tccaaaacaa cctcatcaca gtctccctca accatggcat    360
atatagcttt cttaaccaag ttagtaccaa tgccatttct cctgtatttg              410

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 16
ataacagagg tggccgcgac caca                                            24

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 17
ttatgttcca cttactggtt ctgtgat                                         27

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 18
ggaatccacg gctaacatgg ctat                                            24

<210> SEQ ID NO 19
<211> LENGTH: 2214
<212> TYPE: DNA
<213> ORGANISM: Homo sapiens

<400> SEQUENCE: 19
gaggaggagg aggaagacga gcaggtgcgg ctgctgtctt cgtccctgac cgccgactgc     60
agcttaagaa gcccttcggg cagggaggtt gagcctgggg aggatcggac gatacgatat    120
gtccgatatg aatccgagct acaaatgccc gatatcatga gactgatcac caaagatctg    180
tccgaaccct actccattta tacctataga tattttatcc acaactggcc acagctgtgc    240
ttcttggcca tggtagggga ggagtgtgta ggtgccatcg tttgcaagtt ggatatgcac    300
aaaaagatgt tccgcagagg ttatatagcc atgttagccg tggattccaa atacaggaga    360
aatggcattg gtactaactt ggttaagaaa gctatatatg ccatggttga gggagactgt    420
gatgaggttg ttttggaaac cgaaataaca aataagtccg ctttgaaact ttatgaaaat    480
```

```
-continued cttggttttg ttcgagataa gaggctgttc agatactatt taaatggagt tgatgcactg    540
cgacttaaac tgtggctgcg ttgagaaact gacatcaagg aacaactatc atccacacag    600
aatcgacctt tgcatgcaat gcaatttgta cagaattgct ttgcaggtgg atttagtaat    660
ttccatgcag ctcttacctg tcagtgtctc attgagtgtc gcacaatatt tgttgcactt    720
tggcatggca catttgttct gaattaaaag attgttttaa acttcaggag ttcttttggt    780
accaacaaga tgtgccagtt gatagccaag atttatgtgt tcatttgcaa agtctgctga    840
caatgttatt tacacagtga tcattttatc acagaaccag taagtggaac ataattttg     900 tttccctaaa aagccaatgt ggaattgtaa agtctttaa gtatactaac atttcacaca     960
aaacctgccc tagttttctg aagtgggtga gggagacgct tcagttttag gttttatttt   1020
ttcaatatta aattttccat tcttgaatat tggtacctca gtgattagtg aatgaaaaaa   1080
atgtagggtg ggtatgtctt acaatgagta aaggtaacaa ttaaattttg tctgccagtg   1140
cctgtgtaga taagtatatt tgtcttcatc tccagttttt gaatgcatgc tatcttttcc   1200
ttttctttaa ggcctttgca agcaaacttt tgttttatt taaattctaa atttgataaa    1260
ttatttcaga tttttataat ttggatactt ttttcaggtg aatgaaagaa tggtttactt   1320
tagaagtccc ttttttcctta cagtaacaag ttgaatctac ttggaaaatt gagaaatggc  1380
tcaaaagaga taagaaaagt tgatggagcc gggaattgct ggggttaga tgcacttttt    1440 cttttgagag taagggaagt tttggaaaag aatagaaaat tagtgtaagt tgatatgatt   1500
ttatttaatc aaaattactg ctacgctgcg aagaacagct tttacaaagt agctgaattt   1560 gttttttccca cttgatttgg attcacattg ctttcatttc ttaaaatgct tcacttcagg   1620
ttcttggtct tggaaataaa tttcaaggtg cattgtatcc attttaagct gctttatttt   1680
attttcactt gtatgagcaa attcttgggg gagctttgct tttcttctgc cagaaaaaca   1740 aaaggggaa atgaaaatct tttttggaat gagttctgtg ggttttctta acagccacca    1800
tgtttattag ttacattgtg ttttggccaa tcagtgcaat gtaacaaatt ttacagttaa    1860
ttgctttcaa ttgagtcagt aaacctgtga tagataattt atttaactgg aaaacctagg   1920
tacccataag aaaaaagatt cattctctgt gaaaactgta ggaatctgtt gttgttttca    1980
tttgaatatg ctctacttct gctctagtat ttggtttgga atatattttg tggctctaat   2040
tactgtattt ttaaaaaaac cctacctcca ttaacagttg gtaaaggccc cttttcagga   2100
aagtttgttg ctttttttttt ttttaaagga aagctgctct ctgctcagta tagtgttttg   2160
aaagtgaaca tagtaacaaa tactttaaaa ataaagatac acaatttata tttg          2214
```